United States Patent [19]

Platt et al.

[11] Patent Number: 5,784,294
[45] Date of Patent: Jul. 21, 1998

[54] SYSTEM AND METHOD FOR COMPARATIVE MOLECULAR MOMENT ANALYSIS (COMMA)

[75] Inventors: Daniel Enoch Platt, Bedford Hills; Benjamin David Silverman, Millwood, both of N.Y.

[73] Assignee: International Business Machines Corporation, Armonk, N.Y.

[21] Appl. No.: 489,271

[22] Filed: Jun. 9, 1995

[51] Int. Cl.$^6$ ............................................. G06F 15/46
[52] U.S. Cl. ............................................. 364/496; 364/578
[58] Field of Search ............................. 364/496, 497, 364/500, 578, 499, 554; 395/161

[56] References Cited

U.S. PATENT DOCUMENTS

| | | | |
|---|---|---|---|
| 4,855,931 | 8/1989 | Saunders | 364/499 |
| 5,025,388 | 6/1991 | Cramer, III et al. | 364/496 |
| 5,260,882 | 11/1993 | Blanco et al. | 364/499 |
| 5,331,573 | 7/1994 | Balaji et al. | 364/500 |
| 5,448,498 | 9/1995 | Namiki | 364/496 |

OTHER PUBLICATIONS

Y. Inami et al., "Quantitative Structure–Activity Relationship Analysis of Phencyclidine Derivatives.I" Chem.Pharm. Bull. 39(6) pp. 1426–1429 (1991).

M.C. Cardozo et al., "QSAR Analyses of the Substituted Indanone and Benzylpiperindine Rings of a Series of Indanone–Benzylpiperidine Inhibitors of Acetylcholinesterase" J.Med. Chem. 1992, 35, 584–589.

H. Goldstein, "Classical Mechanics". Addison Wesley, 1980, pp. 158–163, 198–213.

H.H.Harman, "Modern Factor Analysis", Univ. of Chicago Press, 1960 pp. 155–344.

A.M. Goodbody, "Cartesian Tensors: with Applications to Mechanics, Fluid Mechanics and Elasticity", John Wiley and Sons, 1982, pp. 152–164.

R.D.Cramer III et al. "Comparative Molecular Field Analysis (CoMFA). 1.Effect of Shape on Binding of . . . " J.Am.Chem.Soc. V. 110, pp. 5959–5967.

A.C.Good et al. "Structure–Activity Relationships from Molecular Similarity Matrices", J. Med. Chem. vol. 36 1993 pp. 433–438.

A.N.Jain et al. "Compass:Predicting Biological Activities from Molecular Surfaces Properties . . . " J.Med.Chem. V. 37, 1994 pp. 2315–2327.

J.D.Jackson, "Classical Electrodynamics" John Wiley & Sons, 2nd ed., 1975, pp. 136–138.

A.D. Buckingham, "Permanent and Induced Molecular Moments and Long–Range Intermolecular Forces", Adv. in Chem. Physics, V12 pp. 107–141.

C.J. Wylie,Jr., "Advanced Engineering Mathematics" McGraw–Hill Book Co., 2nd Ed., 1960, pp. 37–55.

*Primary Examiner*—Emanuel T. Voeltz
*Assistant Examiner*—Kyle J. Choi
*Attorney, Agent, or Firm*—Jay P. Sbrollini

[57] ABSTRACT

A computer-based method and system describes molecules in a most fundamental and compact way using a set of attributes of the molecule derived from data representing the atomic structure and atomic charge of the molecule. The attributes include the shape of the molecule as defined by the moment of inertia of the molecule, the charge distribution of the molecule as defined by a novel representation of molecular quadrupole, and/or attributes that represent the relationship of the shape to the charge distribution of the molecule. A set of these physical attributes are represented by a set of descriptors. The set of descriptors may be used for molecular matching and activity prediction, as well as in 3D-QSAR analysis.

37 Claims, 7 Drawing Sheets

FIG. 10

| | MEASURED BIOLOGICAL PARAMETER | $D_1$ | $D_2$ | $D_3$ | ... | $D_N$ |
|---|---|---|---|---|---|---|
| MOLECULE 1 | $V_1$ | | | | | |
| MOLECULE 2 | $V_2$ | | | | | |
| MOLECULE 3 | $V_3$ | | | | | |
| | | | | | | |
| MOLECULE OF INTEREST | ? | | | | | |

TABLE

SYSTEM AND METHOD FOR COMPARATIVE MOLECULAR MOMENT ANALYSIS (COMMA)

BACKGROUND OF THE INVENTION

1. Field of the Invention

This invention relates, generally, to comparing molecular shapes and electrostatic charge distributions of different molecules, and, more particularly, to the field of 3D-Quantitative Structure Activity Relations (3-DQSAR) utilized in rational drug design.

2. Description of the Related Art

Understanding the details, at the molecular level, associated with the binding of a potential drug molecule to its targeted receptor site is a fundamental step in the drug discovery process. Such information at the molecular level enables one to search for alternate molecules with similar structural and electrostatic character that will enable the alternate molecules to bind effectively to the receptor site and perhaps exhibit enhanced or optimal biological activity.

For a majority of the cases of interest, ligand-receptor site structural information is not available, i.e., one knows, for example, that a particular molecule, or set of molecules, exhibit a desired biological response but there is no detailed information concerning how such a molecule binds to its target site. Furthermore, in many cases the target site is unknown. A rational drug discovery strategy to address this scenario has been to search for other molecules that are structurally and electrostatically similar to the biologically active molecule or molecules that have been identified in a blind or other screen.

A detailed discussion of 3D quantitative structure activity relations (3-DQSAR) prior art and background material can be found in U.S. Pat. No. 5,025,388 to R. D. Cramer and S. B. Wold, entitled "Comparative Molecular Field Analysis" (COMFA patent). The COMFA patent describes the utilization of a drug discovery algorithm involving statistical as well as graphical implementation. More particularly, the drug discovery algorithms of the COMFA patent involve molecular comparison within the context of 3-DQSAR. 3-DQSAR involves descriptions of molecular shape and charge, which in turn relates to the biological activity of the molecules. Since non-bonding interactions are usually the majority of the interactions involved in ligand-receptor binding, molecular steric and electrostatic features are predominantly involved in the bonding.

A typical sequence of steps used in the prior art is schematically illustrated in FIG. 5 of the COMFA patent.

Prior to the determination of molecular shape/steric and charge/electrostatic descriptors, the three dimensional structure of the molecule must be determined. This is achieved by obtaining structures from a three dimensional database such as the Cambridge Structure File or by generating structures that are consistent with general chemical principles. The latter procedure can be accomplished with utilization of appropriate software code, for example SYBYL provided by Tripos, Inc. of St. Louis, Mo., INSIGHT provided by BIOSYMM, Inc. of San Diego, Calif., and CHARMM provided by Molecular Simulations, Inc. of Burlington, Mass.

After determination of the molecular structures, atomic charges or other molecular features, molecular alignment is then performed. This can be achieved by overlaying each pair of molecules and translating and rotating them with respect to each other until an optimal fit is obtained. The "fit" is achieved with respect to structural and/or electrostatic molecular features.

Subsequent to molecular alignment, descriptors of molecular shape and charge distributions responsible for steric and electrostatic interactions are determined. This can be achieved in several different ways. For example, in the COMFA patent, a grid may be superposed on the molecule and steric and electrostatic energies assigned to each of the grid points (see also, "Comparative Molecular Field Analysis (COMFA) Effect of Shape on Binding of Steroids to Carrier Proteins", R. D. Cramer, D. E. Patterson, and J. D. Bunce, J. AM. Chem. Soc. Vol. 110, 1988, pp. 5959–5967. Similarity matrices may be developed which are determined from the overlap of molecular density and charge distributions (see A. C. Good, S. S. So, and W. G. Richards, "Structure Activity Relationships from Molecular Similarity-Matrices", J. Med. Chem. Vol. 36, 1993, pp. 433–438) or molecular surface descriptors may be obtained by referencing steric features such as van der waals surfaces and electrostatic features such as hydrogen bonding donor and acceptor locations to a set of sampling points (see A. N. Jain, K. Koile, D. Chapman, "Compass: Predicting Biological Activities from Molecular Surface Properties, Performance Comparisons on a Steroid Benchmark", J. Med. Chem. Vol. 37, 1994, pp. 2315–2327). Shape descriptors have been determined by utilizing electron densities, van der waals surfaces or values of van der waals/steric (e.g. 6–12) potentials. Charge descriptors have been determined by utilizing either point charge distributions at atomic sites and/or consequent electrostatic potentials or by hydrogen bond donor-acceptor locations.

Having determined a set of molecular steric/electrostatic descriptors that span a 3 dimensional space in the vicinity of each of the molecules, one may utilize the descriptors to determine the multiple regression coefficients that enable prediction of an unknown biological property of a molecule that is not part of a training set (i.e., molecules for which a particular biological property is known).

For the circumstances usually encountered in previous 3-DQSAR studies, the multiple regression coefficients are underdetermined since the number of descriptors is greater than the number of molecules in the training set. Thus, special procedures are required to determine the multiple regression coefficients. One of such special procedures, Partial Least Squares (PLS) analysis may be found in the COMFA patent cited above. PLS analysis provides a statistical determination of the regression coefficients for such underdetermined set of equations. Another procedure for determining the multiple regression coefficients utilizes neural network analysis such as described in the Good and Jain references cited above.

Finally, after determining the regression coefficients, graphical outputs are provided to the user that demonstrate the results obtained from the analysis.

3. Statement of the Problems of the Prior Art

The prior art requires a molecular alignment step in order to calculate descriptors and/or prior to making a comparison between molecules. The molecules must be superimposed and then rotated and translated with respect to each other during which time a calculation for each relative orientation must be performed to provide a measure of comparison. Such calculation might involve a comparison of shape, specific locations of several specified atoms on the respective molecules, or the electrostatic fields generated by the molecules. This is a time consuming step which imposes time constraints on the number of molecules examined.

After such alignment is performed, the relevant molecular descriptors can then be calculated. There is, furthermore, no guarantee that the alignment has been performed appropriately (i.e., the molecules have been aligned in a manner which corresponds the orientation that they present to the target receptor site).

In general, the prior art has required special statistical handling for a system of equations that are underdetermined with respect to the determination of regression coefficients (i.e., there are more unknown regression coefficients than there are equations. Some of the prior art uses principal components analysis (PCA), or more commonly called Partial Least Squares (PLS) analysis. PLS evaluates a model not by how well it fits data, but by how well it predicts data. In other words, spurious results might occur by using PLS and this has been the subject of discussion in the literature.

It is generally agreed that steric and electrostatic non-bonding interactions are the predominant three dimensional determinants of ligand-receptor binding, the binding that is fundamental to drug interactions with biological systems. These interactions have been described and calculated in various ways in the several drug discovery systems that have either been described in the professional literature or are vended by third party application solution providers, i.e., TRIPOS, BIOSYM, MOLECULAR SIMULATIONS, etc. All of these programs do not treat the three dimensional character of molecular steric and electrostatic interactions in the simplest and most fundamental manner that can be utilized for 3-DQSAR as well as for more general procedures involving molecular comparison.

SUMMARY OF THE INVENTION

An object of the invention is to provide a fundamental method for the comparison of molecular shape (steric) and electrostatic charge without the requirement of molecular alignment.

Another object of the invention is an improved system and method for the rapid prediction of the biological activity of a molecule or set of molecules from data stored in a database.

Another object of the invention is to provide a set of descriptors that represent the shape and/or charge distribution of a molecule that are independent of the position and orientation of the molecule in space.

Another object of the invention is to provide unique internal alignment information with respect to which descriptions and comparisons of structure, field and shape may be made.

Another object of the invention is to provide a reference frame, e.g. principal inertial or quadrupolar axes with respect to which local descriptors may be referenced. For example a COMFA grid may be with respect to either of the reference frames.

According to the present invention, molecules are described in a most fundamental and compact way using a set of physical attributes of the molecule. The attributes include the shape of the molecule as defined by the moment of inertia of the molecule, the charge distribution of the molecule as defined by a novel representation of molecular quadrupole, and/or attributes that represent the relationship of the shape to the charge distribution of the molecule. A set of these physical attributes are represented by a set of descriptors. The set of descriptors may be used for molecular matching and activity prediction.

Because both the shape attributes and charge attributes of the molecule, as well as their relationships, are independent of the position and orientation of the molecule in space, an alignment step is not required when comparing two or more molecules. Thus, the descriptors of the present invention enable a simple, very rapid comparison between different molecules.

Moreover, the descriptors of the present invention can-be used with 3-DQSAR calculations to predict the biological activity of molecular structures that have not been experimentally examined for such activity; and, because the set of descriptors is sufficiently small, in many situations standard multivariate regression analysis can be used in the 3-DQSAR, without using the more complex and time-consuming PLS analysis with a massive number of descriptors. In any event, the small number of internal descriptors of the present invention militates for a rapid analysis of the data.

Other objects, features, and advantages of the invention will become apparent in light of the following description presented in conjunction with the accompanying drawings.

BRIEF DESCRIPTION OF THE DRAWINGS

FIG. 10 is a table illustrating the use of the descriptors of the present invention in 3-DQSAR analysis.

DETAILED DESCRIPTION OF THE INVENTION

Figure 1:
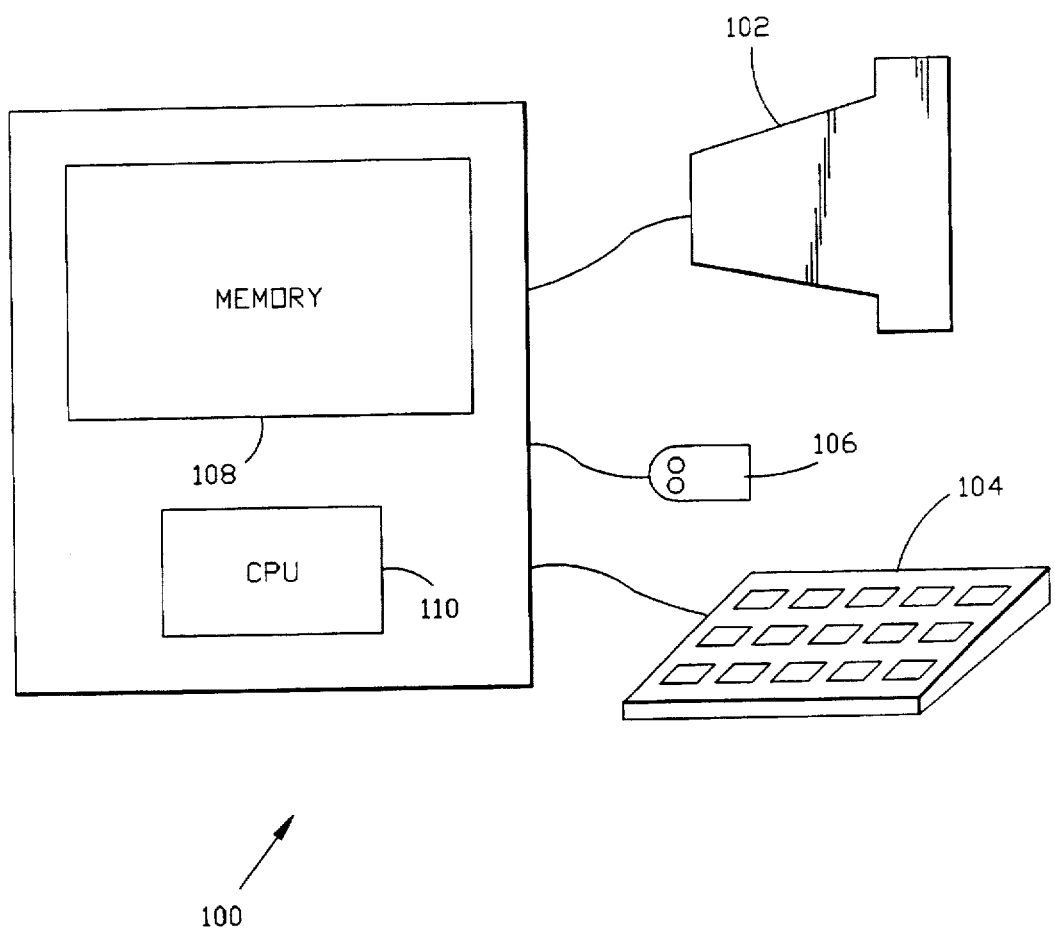
FIG. 1 is a block diagram of a computer processing system that embodies the invention.

FIG. 1 is a functional block diagram of a general purpose computer system 100 that embodies the present invention. The computer system 100 may include a work station (or high performance personal computer) that performs the relevant calculations as discussed below, e.g., calculations involving the structure and electronic charge of molecules. For example, the computer system 100 may be an IBM RS/6000 with a graphical interface 102, user input devices such as a keyboard 104 and mouse 106. The computer system 100 also includes a memory 108 that stores the software applications that are executed on a processor 110 to perform the molecular model building, molecular simulations, and required statistical analyses as discussed below. For example, the software which provides the necessary environment for the present invention may include SYBYL, release 6.01, available from TRIPOS, Inc. If the SYBYL environment is not used, equivalent software applications may be stored in the memory 108. For example, high level approximations to molecular dipoles and quadrupoles may be calculated utilizing ab-initio quantum chemistry procedures. To do these calculations, software applications such as GAUSSIAN '92, HONDO, SPARTAN, may be stored in the memory 108.

According to the present invention, a set of physical attributes that describe a molecule may be determined from data representing the atomic structure of the molecule as stored in the memory 108. The physical attributes include the shape of the molecule as characterized by the moment of inertia of the molecule, the charge distribution of the molecule as characterized by the dipole moment of the molecule and a novel representation of molecular quadrupole, and/or attributes that represent the relationship of the shape to the charge distribution. The description below first outlines techniques to determine the moment of inertia of a molecule and the charge distribution of the molecule, and secondly outlines how these attributes can be mapped to descriptors that are used to compare molecules, for example, in 3-DQSAR calculations.

The moment of inertia is a physically measurable quantity of a body, e.g. a molecule. Analogous with total molecular mass (which determines how the center of gravity of a molecule will accelerate when subject to a given force), the moment of inertia of a molecule determines how the angular velocity changes about the center of mass when the molecule is subject to a given torque. Importantly, the moment of inertia of a given molecule is descriptive of the shape and mass distribution of the molecule.

The moment of inertia of a molecule may be characterized by a set of numbers that transform as a second rank tensor I. The moment of inertia tensor I relates the angular velocity of the molecule to its angular momentum in a frame of reference (u1, u2, u3) fixed with respect to the center of mass of the molecule. If the angular velocity of the molecule is $\vec{\omega}$, then the angular momentum is:

$$\vec{L} = I\vec{\omega}$$

Second rank tensors have principle vectors (also called eigenvectors or proper vectors). These vectors are characterized as being in the same direction after being operated on by the tensor. In the case of the moment of inertia tensor I, the principle vectors correspond to directions such that the angular velocities are parallel to their angular momenta. In other words, $$\vec{L} = I\vec{\omega} = I'\vec{\omega}$$

for some scalar values I1,I2,I3 called the principal values. Hereinafter, these principle values I1,I2,I3 are called the principle components of the moment of inertia of the molecule. A more detailed description of the derivation of the moment of inertia tensor and its principal components may be found in "Cartesian Tensors", by A. M. Goodbody, pp. 152–203, John Wiley and Sons, 1982, and "Classical Mechanics", by H. Goldstein, pp. 198–213, Addison Wesley, 1980, herein incorporated by reference in their entirety.

The principle components I1,I2,I3 of the moment of inertia tensor I each align along one of the directions of a coordinate system (x,y,z), called the inertial coordinate system. In the inertial coordinate system, any angular velocity about a coordinate axis (x,y,z) results in a molecular angular momentum parallel to the molecular angular velocity. The coordinate axes (x,y,z) are called principle inertial axes, and the moment of inertia tensor I has all off diagonal elements equal to zero and its diagonal elements equal to the principle components of moment inertia, I1, I2, and I3 along the x, y, and z axes, respectively.

Effects of angular velocity about one or more principle inertial axes can be illustrated in the dynamical balancing of the tire of a wheel. If the tire is not dynamically balanced, the angular momentum is not lined up with the axis of rotation. Here the axis of rotation is the axle of the wheel and the principle axis is determined by the weight distribution and shape of the tire/wheel combination. The unbalanced case requires a torque $$\vec{N} = d\vec{L}/dt$$

to maintain the axle as the axis of rotation. This may produce an unpleasant and mechanically damaging vibration. When the tires are dynamical balanced, the principle axis of the tire/wheel combination is coincident with the axle. In the balanced case, there is no vibration caused by the wheel rotation.

Figure 2:
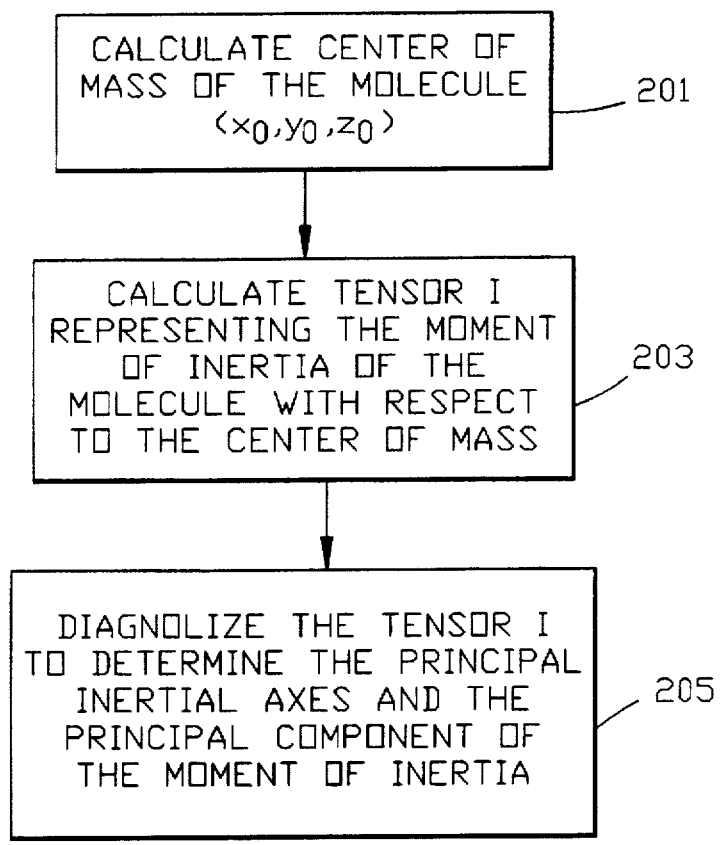
FIG. 2 is a flow chart illustrating the steps to determine the principal inertial axes and principal components of the moment of inertia of a molecule according to the present invention.
Figure 3:
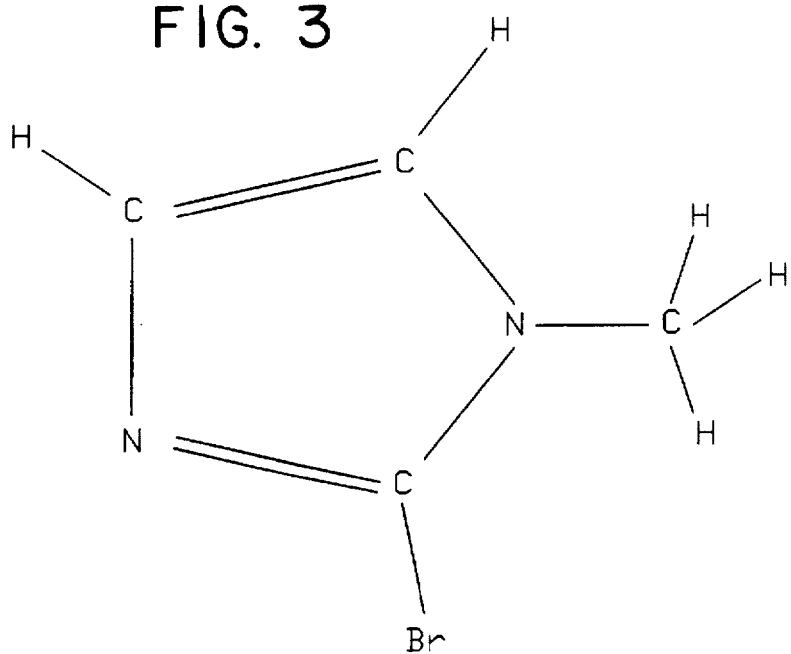
FIG. 3 is a two-dimensional representation of an IMIDIZOLE molecule.

FIG. 2 illustrates the steps performed in determining the principal axes and the principle components I1,I2,I3 of the moment of inertia of a molecule according to data representing the atomic structure of the molecule stored in the memory 108. In step 201, the center of mass of the molecule, denoted by the expression $(x_0, y_0, z_0)$, is determined. For example, consider the IMIDAZOLE molecule as shown in FIG. 3. The IMIDAZOLE molecule may be represented by the following data as stored in the memory 108:

| Atom | Coordinates of Nucleus | | | charge (units of electron charge) | atomic weight |
|------|---|---|---|---|---|
| | x (Å) | y (Å) | z (Å) | | |
| N  | 0.6662  | 0.6445  | −0.0000 | −0.2876 | 14.006700 |
| C  | 1.0836  | −0.5855 | −0.0000 | 0.1690  | 12.011150 |
| N  | 0.1003  | −1.3631 | −0.0000 | −0.2321 | 14.006700 |
| C  | −1.1229 | −0.6085 | −0.0000 | 0.0442  | 12.011150 |
| C  | −0.6499 | 0.6537  | −0.0000 | 0.0164  | 12.011150 |
| C  | 1.4974  | 1.8448  | −0.0000 | 0.0071  | 12.011150 |
| BR | 2.8787  | −1.1838 | −0.0000 | −0.0109 | 79.909000 |
| H  | −2.1515 | −0.9668 | −0.0000 | 0.0843  | 1.007970 |
| H  | −1.2766 | 1.5455  | −0.0000 | 0.0799  | 1.007970 |
| H  | 2.5746  | 1.6229  | −0.0000 | 0.0432  | 1.007970 |
| H  | 1.2674  | 2.4428  | 0.8950  | 0.0432  | 1.007970 |
| H  | 1.2674  | 2.4428  | −0.8950 | 0.0432  | 1.007970 |

The center of mass $(x_0, y_0, z_0)$ of the IMIDAZOLE molecule may be determined utilizing the data stored in the memory 108 according to the following equations:

$$x_0 = \frac{\Sigma m_i x_i}{M}$$

$$y_0 = \frac{\Sigma m_i y_i}{M}$$

$$z_0 = \frac{\Sigma m_i z_i}{M}$$

where $m_i$ is the mass of each atom that makes up the IMIDAZOLE molecule, and M is the total mass of the IMIDAZOLE molecule which may be represented by the equation $M = \Sigma m_i$.

In this case, the center of mass $(x_0, y_0, z_0)$ of the IMIDAZOLE molecule is (1.566221 Å, −0.508359 Å, 0.00000 Å). In step 203, the second rank tensor I representing the moment of inertia of the IMIDAZOLE molecule with respect to that center of mass is determined. For example, the diagonal terms of the tensor I may be determined with respect to a set of arbitrary Cartesian axes (e1, e2, e3) whose origin is at the center of mass of the molecule according to the following equations:

$$I_{11} = \int_V \rho(r)(x_2^2 + x_3^2)dV$$

$$I_{22} = \int_V \rho(r)(x_3^2 + x_1^2)dV$$

$$I_{33} = \int_V \rho(r)(x_1^2 + x_2^2)dV$$

wherein $I_{11}, I_{22}, I_{33}$ represent the moment of inertia of the IMIDAZOLE molecule about the e1, e2, e3 axes, respectively, and $\vec{r}$ is the vector between the center of mass of the IMIDAZOLE molecule and the atoms of the IMIDAZOLE molecule.

The off-diagonal terms of the tensor I may be determined with respect to the axes (e1, e2, e3) according to the following equations:

$$I_{12} = I_{21} = -\int_V \rho(r)x_1 x_2 dV$$

$$I_{13} = I_{31} = -\int_V \rho(r)x_1 x_3 dV$$

$$I_{23} = I_{32} = -\int_V \rho(r)x_2 x_3 dV$$

Preferably, the mass distribution of the molecule is simplified by treating each atom of the molecule as a point mass located at the nucleus of the particular atom. In this case, the integrals defining the moment of inertia tensor of the molecule may be determined as the sum of the terms as set forth above, wherein each term is related to a particular atom of the molecule. In the example, the second rank tensor I of the IMIDAZOLE molecule becomes $$I = \begin{bmatrix} 176.441428 & 100.796926 & 0.00000 \\ 100.796926 & 352.694759 & 0.00000 \\ 0.00000 & 0.00000 & 525.906550 \end{bmatrix} Å^2$$

In step 205, the second rank tensor I is diagonalized in order to obtain the principal components (I1, I2, I3) of the moment of inertia as well as the orientation of the principal inertial axes (x,y,z) in space. To diagonalize the matrix, one may use the techniques described in C. R. Wylie, Jr., "Advanced Engineering Mathematics," McGraw-Hill Book Co., 2nd Ed., 1960, pp. 37–55, and "Classical Mechanics", by H. Goldstein, pp. 158–163, Addison Wesley, 1980, herein incorporated by reference in their entirety. In the example, the principal components I1,I2,I3 of the moment of inertia of the IMIDAZOLE molecule are (130.678850, 398.457337, 525.906550) Å$^2$, and the orientation with respect to the initial frame of the principal inertial axis x is (0.910551, −0.413397, 0.00000), the orientation with respect to the intitial frame of the principal inertial axis y is (0.413397, 0.910551, 0.00000), and the orientation with respect to the intitial frame of the principal inertial axis z is (0.00000, 0.00000, 1.0000).

According to the present invention, the set of physical attributes that describe a molecule include the charge distribution of the molecule as characterized by a novel representation of molecular quadrupole as determined from data representing the atomic structure of the molecule stored in the memory 108. The charge distribution of the molecule is-important in predicting molecular interaction. For example, in drug design, the charge distribution of a particular molecule will dictate the interaction of the molecule when subject to the electric field created at a "docking location" of a second molecule. Furthermore, electromagnetic radiation is coupled to molecular charge distribution through the dipole and higher order moments. Moreover, most spectroscopic measurements in analytical chemistry involve static or induced dipole moments.

The unique representation of the multipolar electrostatic potential expansion of the molecule proposed in this invention is dependent upon the type of molecule (i.e., is the molecule ionic, neutral-polar, neutral-nonpolar-quadrupolar). Importantly, molecular type is dictated by the leading non-vanishing term of the multipolar expansion.

Figure 4:
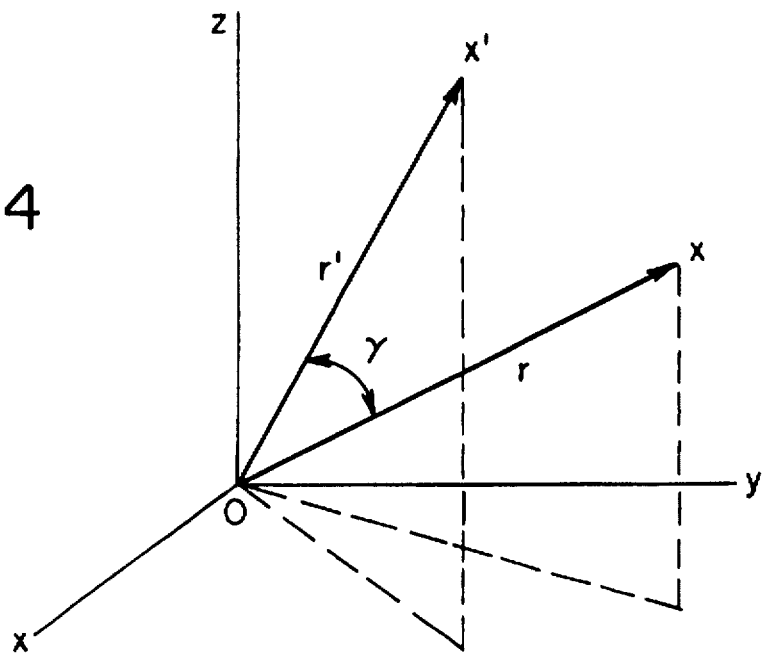
FIG. 4 is a pictorial representation of the coordinate system utilized to calculate the electric potential $\phi$ of a molecule according to the present invention.

The charge distribution of the molecule determines the electric field potential in the vicinity of the molecule. More specifically, with reference to FIG. 4, the field potential $\phi(x)$ at a point x outside a molecule in which electrical charges are distributed with a density $\rho = \rho(x')$ may be expressed by the integral:

$$\phi(\vec{x}) = \int_V \frac{\rho(\vec{x'})}{|\vec{x} - \vec{x'}|} d^3x'$$

wherein x is a distance r from an arbitrary initial point of expansion O, and x' is a distance r' from the point of expansion O to an element of charge.

Taylor series techniques may be utilized to represent the expansion of the field potential $\Phi(x)$ in a series on powers of 1/r, conventionally called the multipolar expansion, as:

$$\phi(\vec{x}) = \frac{q}{r} + \frac{\vec{p} \cdot \vec{x}}{r^3} + \frac{1}{2} \Sigma Q_{ij} \frac{x_i x_j}{r^5} + \ldots$$

wherein q is the total charge or monopole moment p is the electric dipole moment given by:

$$\vec{p} = \int_V \vec{x'} \rho(\vec{x'}) d^3x'$$

and $Q_{ij}$ is a traceless quadrupole moment tensor given by:

$$Q_{ij} = \frac{1}{2} (3x'_i x'_j - r'^2 \delta_{ij}) \rho(\vec{x'}) d^3x'$$

The higher order terms not explicitly shown in the multipolar expansion include an octupole moment, etc. A more detailed description of the mathematics required to derive the equations above may be found in "Classical Electrodynamics", by Jackson, pp. 136–138, John Wiley and Sons, 2nd ed., 1975, and "Permanent and Induced Molecular Moments and Long Range Intermolecular Forces", by A. D. Buckingham, Advances in Chemical Physics, Vol. 12, pp. 107–141, 1967, herein incorporated by reference in their entirety.

Figure 5:
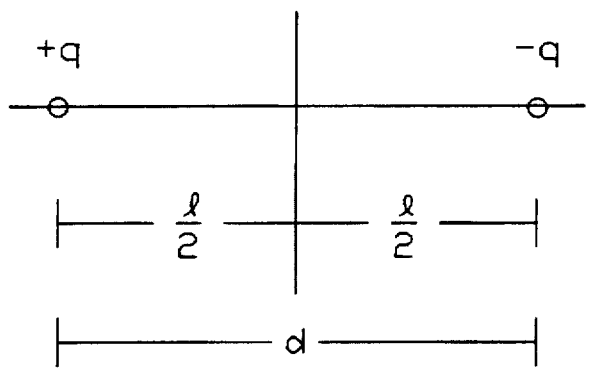
FIG. 5 is a representation of a simple dipole.

Thus, the first three terms of the multipolar expansion of a charge distribution involve: the total charge (or monopole moment), the dipole moment, and the quadrupole moment. FIG. 5 is a schematic diagram illustrating the concept of molecular dipole. More specifically, a simple representation of molecular dipole includes two charges of equal magnitude and opposite sign separated by a distance as shown. In this simple case, the dipole moment of the molecule is given as $-qd$.

Figure 6:
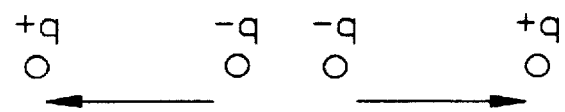
FIG. 6 is a representation of a simple quadrupole.

A simple representation of a quadrupole is shown in FIG. 6. As shown, two identical dipoles are placed head to tail such that the net dipole moment is zero, as well as the net charge. However, in a more general sense, the quadrupole moment of a molecule represents the higher order effects of groupings of dipoles separated by various distances with the constraint that the net molecular dipole moment remain zero.

The point of expansion O as described above is arbitrary. Consider a vector $\vec{x}$ with O as the origin related to a vector $\vec{x}'$ with O' as the origin via:

$$\vec{x}' = \vec{x} - \vec{x}_o$$

For the case of non-vanishing moments of all orders for the expansion about O, $$q' = q;$$

$\vec{p}'$ is the electric dipole moment given by:

$$\vec{p}' = \vec{p} - q\vec{x}_o$$

and $Q'_{ij}$ is a traceless quadrupole moment tensor given by:

$$Q'_{ij} = Q - (3\vec{x}_o \vec{p} + 3\vec{p}\vec{x}_o - 2\vec{x}_o \cdot \vec{p} I) + q(3\vec{x}_o \vec{x}_o - |\vec{x}_o|^2 I)$$

Note that for neutral molecules ($q=0$), the dipole moment does not change upon translation of the origin of expansion, yet the quadrupole moment does change. This implies that the multipole moments of higher order than the lowest non-vanishing term depend upon the point of expansion. For this reason, the prior art avoided utilizing the quadrupole moment of molecules with vanishing net charge as a descriptor of charge.

For descriptive purposes only, consider a neutral molecule wherein the dipolar moment contribution is the leading nonvanishing term of the multipolar electrostatic potential expansion (i.e., N=1). For this case, the present invention avoids this limitation of the quadrupole moment by defining a term called the "center of dipole". Importantly, determining the quadrupolar moment tensor about the center of dipole enables one to compare the components of the quadrupolar moment tensor of molecules of arbitrary structure or symmetry. More specifically, the "center of dipole" is defined as the point in space wherein the contribution of the quadrupolar moment to the leading term of the total solid angle square residue (TSASR) is minimized. The TSASR is given by:

$$\int d\Omega |\phi(\vec{x}) - \phi_N(\vec{x})|^2$$

wherein $\phi_N(\vec{x})$ is the leading non-zero multiploar contribution to $\phi(\vec{x})$. For the present example (i.e., neutral polar molecules), N=1.

To determine the point in space wherein the contribution of the quadrupolar term to the leading term of the TSASR is minimized, note that the leading term of the TSASR involves the quadrupolar components, denoted $q_{2m}$, where $$\sum_m |q_{2m}|^2 = \frac{5}{24\pi} \sum_{ij} |Q_{ij}|^2$$

wherein $Q_{ij}$ is the traceless Cartesian representation of the quadrupolar moment tensor about the arbitrary point of expansion O as described above.

If the displacement from the arbitrary point of expansion O to the center of dipole is given as a vector $\vec{d}$, values of the vector $\vec{d}$ can be solved for as follows.

The value of the quadrupolar moment of inertia tensor $Q'$ at a location O', wherein $O' = O + \vec{d}$, may be represented by the expression:

$$2Q' = 2Q - (3\vec{d}\vec{p} + 3\vec{p}\vec{d} - 2\vec{p} \cdot \vec{d} I)$$

such that $$2\frac{\partial Q'_{ij}}{\partial d_k} = -3p_i\delta_{jk} - 3p_j\delta_{ik} + 2p_k\delta_{ij}$$

Thus, determining the position wherein the contribution of the quadrupolar moment to leading term of the TSASR is minimized is obtained by imposing:

$$\frac{\partial}{\partial d_k} \sum_m |q_{2m}|^2 = -\frac{5}{\pi} \sum_i Q'_{ki} p_i = 0$$

or $$2Q' \cdot \vec{p} = 2Q \cdot \vec{p} - \vec{p}(\vec{p} \cdot \vec{d}) - 3p^2 \vec{d} = \vec{0} \qquad (i)$$

This may be solved for $\vec{d}$ by first solving for $\vec{p} \cdot \vec{d}$, which may be achieved by dotting equation (i) with $\vec{p}$ to yield:

$$\vec{p} \cdot \vec{d} = \frac{\vec{p} \cdot Q \cdot \vec{p}}{2p^2}$$

Substituting this into equation (i) and solving for $\vec{d}$ yields:

$$\vec{d} = \frac{2}{3p^2} \left[ Q \cdot \vec{p} - \left( \frac{\vec{p} \cdot Q \cdot \vec{p}}{4p^2} \right) \vec{p} \right]$$

wherein $\vec{p}$ is the dipole moment and Q is the quadrupole moment tensor calculated about the initial arbitrary point of expansion as described above.

Figure 7:
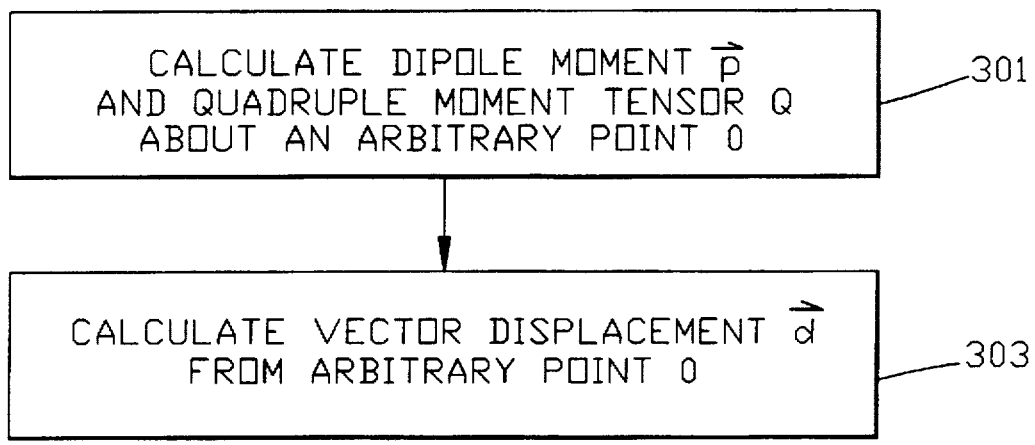
FIG. 7 is a flow chart illustrating the steps to determine the center of dipole according to the present invention.

The steps to determine the center of dipole are illustrated in detail in FIG. 7. For illustrative purposes, consider again the IMIDAZOLE molecule. In step 301, the dipole moment $\vec{p}$ and quadrupole moment tensor Q are determined about the arbitrary point of expansion O according to data representing the atomic structure and atomic charge of the IMIDAZOLE molecule stored in the memory 108. As discussed above, the dipole moment p is determined by:

$$\vec{p} = \int \vec{x}' \rho(\vec{x}') d^3x'$$

and the quadrupole moment tensor Q is given by:

$$Q_{ij} = \frac{1}{2} \int (3x'_i x'_j - r'^2 \delta_{ij}) \rho(\vec{x}') d^3x'$$

The charge distribution of the molecule may be simplified by treating each atom of the molecule as a point charge located at the nucleus of the particular atom. In this case, the integrals that define the dipole moment p and the quadrupole moment tensor Q are determined as a sum of the terms as set forth above, wherein each terms relates to each atom of the molecule. In the alternative, the integrals that define the dipole moment p and the quadrupole moment tensor Q may be determined using ab-initio quantum chemistry application software such as GAUSSIAN '92, available from Gaussian, Inc. of Pittsburg, Pa. In the example, the dipole moment $\vec{p}$, calculated with Gasteiger point charges, is:

$$\vec{p} = (-0.175382, 0.365100, -0.00000)$$

In step 303, the vector displacement from the arbitrary point of expansion O to the center of dipole is determined using the equation presented above:

$$\vec{d} = \frac{2}{3p^2}\left[Q \cdot \vec{p} - \left(\frac{\vec{p} \cdot Q \cdot \vec{p}}{4p^2}\right)\vec{p}\right]$$

For the IMIDAZOLE molecule, $\vec{d}$ is (0.176883, −0.387081, 0.0). If need be, the coordinates of the center of dipole may be determined by adding the vector displacement $\vec{d}$ to the coordinates of the arbitrary point of expansion O.

Figure 8:
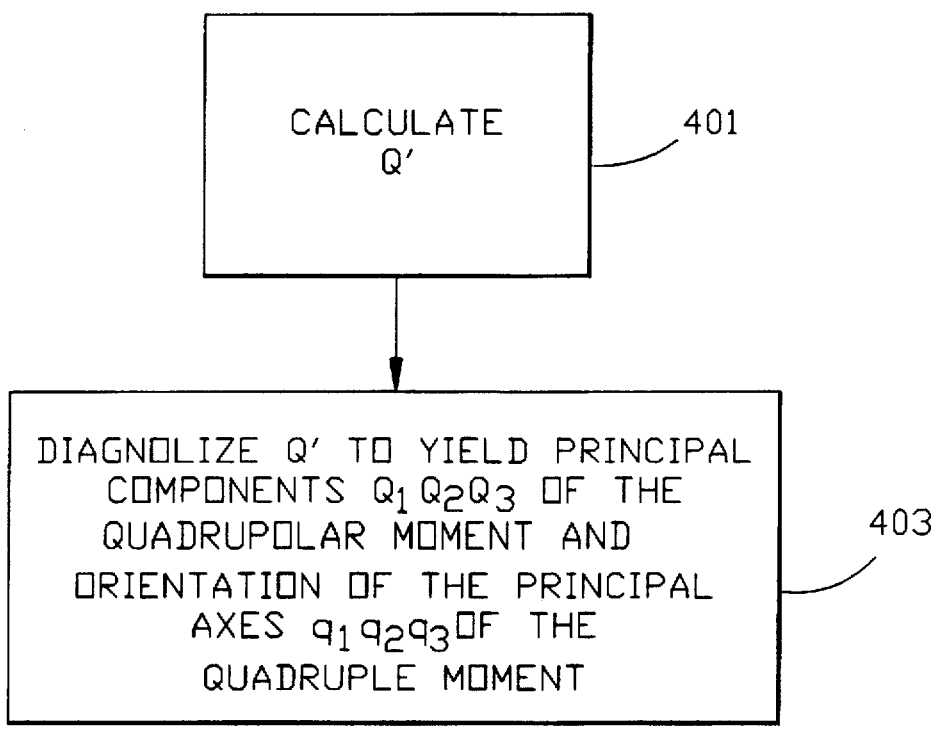
FIG. 8 is a flow chart illustrating the steps to determine the principal axes and principal components of the quadrupolar contribution to the multipolar expansion of the potential p at the center of dipole according to the present invention.

Having determined the vector displacement $\vec{d}$ of the center of dipole from the arbitrary point of expansion O, the quadrupolar moment tensor Q' at the center of dipole may be determined from the charge distribution of the molecule. A more detailed description of the steps in determining the quadrupolar moment Q' at the center of dipole is illustrated in FIG. 8. In step 401, the quadrupolar moment Q' at the center of dipole is determined according to the quadrupolar moment tensor Q, the dipole moment $\vec{p}$, and the vector displacement $\vec{d}$ as follows:

$$Q' = \frac{1}{2}Q - \frac{1}{2}(3\vec{d}\vec{p} + 3\vec{p}\vec{d} - 2\vec{p} \cdot \vec{d} I)$$

For the IMIDAZOLE molecule, in a Cartesian reference frame with the origin at the center of dipole but un-rotated with respect to the initial arbitrary frame, Q' becomes:

$$Q' = \begin{bmatrix} 1.338591 & 0.643015 & 0.00000 \\ 0.643015 & 0.308883 & -0.00000 \\ -0.00000 & -0.00000 & -1.647474 \end{bmatrix}$$

In step 403, the quadrupolar moment tensor Q' is diagonalized in order to obtain the principal components (Q1, Q2, Q3) of the quadrupolar moment tensor Q' as well as the orientation of the principal axes (q1,q2,q3) of the quadrupolar moment tensor Q' in space. To diagonalize the matrix, one may use the techniques described in C. R. Wylie, Jr., "Advanced Engineering Mathematics," McGraw-Hill Book Co., 2nd Ed., 1960, pp. 37–55, and "Classical Mechanics", by H. Goldstein, pp. 158–163, Addison Wesley, 1980, incorporated by reference above in their entirety. In the example, the principal components (Q1,Q2,Q3) of the quadrupolar moment tensor Q' of the IMIDAZOLE molecule are (−1.647474, 0.00000, 1.647474), the orientation with respect to the initial frame of the principal axis q1 of the quadrupolar moment tensor Q' is (0.000000, 0.00000, 1.00000), the orientation with respect to the intitial frame of the principal axis q2 of the quadrupolar moment tensor Q' is (0.433000, −0.901394, 0.000000), and the orientation with respect to the intitial frame of the principal axis q3 of the quadrupolar moment tensor Q' is (0.901394, 0.433000, 0.00000). Note that one of the principal components Q1,Q2, Q3 of the quadrupolar moment tensor Q' is zero, while the other two are equal in magnitude yet opposite in sign. This results from the solutions of the equation $Q' \cdot \vec{p} = 0$. In addition, the particular nature of this equation constrains the dipole to a point along the quadrupolar principal axis associated with zero magnitude. Thus, the two non-zero principal components of the quadrupolar moment Q' are equal in magnitude and opposite in sign as a consequence of the tracelessness of the quadrupolar tensor. This, therefore, yields a single quadrupolar descriptor associated solely with the charge distribution of the molecule that may be utilized in 3-DQSAR analysis.

In addition, the magnitude of the dipole moment $\vec{p}$ may be utilized as a descriptor that characterizes the charge distribution of a molecule. The magnitude of the dipole moment $\vec{p}$ may be determined as:

$$|\vec{p}| = \sqrt{p_x^2 + p_y^2 + p_z^2}$$

Thus, in the example, the components of the dipole moment $\vec{p}$ of the IMIDAZOLE molecule in the original frame are (−0.175382, 0.365100, −0.00000) and the magnitude of the dipole moment is 0.405039 Å.

According to the present invention, additional descriptors may be determined that characterize the relationship between the shape descriptors and charge descriptors as described above. The descriptors may be divided into two groups: a first group related to the inertial coordinate system defined by the inertial axes x,y,z, and a second group related to the coordinate system defined by the axes q1,q2,q3 (hereinafter referred to as the quadrupolar coordinate system).

One of the descriptors of the first group is the projection of the dipole moment $\vec{p}$ onto the inertial axes (x,y,z), which may be determined as follows:

$$P_x = \vec{p} \cdot \hat{x}, \quad P_y = \vec{p} \cdot \hat{y}, \quad P_z = \vec{p} \cdot \hat{z}$$

wherein $\hat{x}$, $\hat{y}$, $\hat{z}$ are unit vectors in the direction of the inertial axes x,y,z respectively.

For the IMIDAZOLE molecule, the projections $P_x, P_y, P_z$ are (−0.310625, 0.259940, −0.0000).

Another descriptor belonging to the first group is the traceless quadrupolar moment tensor Q' calculated about the center of dipole referenced to the unit vectors $\hat{x}$, $\hat{y}$, $\hat{z}$ translated such that the origin of the inertial axes x,y,z coincides with the center of dipole. This particular descriptor consists of three diagonal components and three off-diagonal components. The diagonal terms of the quadrupolar moment tensor Q' may be determined with respect to the set of inertial axes x,y,z whose origin is at the center of dipole of the molecule according to the following equations:

$$Q'_{11} = \frac{1}{2}\int \rho(\vec{x})(3x^2 - x^2 - y^2 - z^2)d^3x$$

$$Q'_{22} = \frac{1}{2}\int \rho(\vec{x})(3x^2 - x^2 - y^2 - z^2)d^3x$$

$$Q'_{33} = \frac{1}{2}\int \rho(\vec{x})(3x^2 - x^2 - y^2 - z^2)d^3x$$

wherein $Q'_{11}$, $Q'_{22}$, $Q'_{33}$ represent the quadrupolar moment of the molecule, $\rho$ is the charge density of the molecule, and $\vec{x}$ is the vector between the center of dipole of the molecule and the atomic charges of the molecule.

The off-diagonal terms of the tensor Q' may be determined according to the following equations:

$$Q'_{12}=Q'_{22}=\tfrac{1}{2}\int \rho(\vec{x})\,(3xy)\,d^3x$$

$$Q'_{13}=Q'_{31}=\tfrac{1}{2}\int \rho(\vec{x})\,(3xy)\,d^3x$$

$$Q'_{23}=Q'_{32}=\tfrac{1}{2}\int \rho(\vec{x})\,(3xy)\,d^3x$$

For the IMIDAZOLE molecule,
$Q'_{11}=0.678531\ \text{Å}^2$
$Q'_{12}=0.810838\ \text{Å}^2$
$Q'_{13}=0.000000\ \text{Å}^2$
$Q'_{22}=0.968943\ \text{Å}^2$
$Q'_{23}=0.000000\ \text{Å}^2$
$Q'_{33}=-1.647474\ \text{Å}^2$ Another descriptor belonging to the first group is the vector displacement of the center of mass of the molecule from the center of dipole of the molecule in the inertial coordinate system.

One of the descriptors of the second group is the projection of the dipole moment $\vec{p}$ onto the unit vectors $\hat{q}_1$, $\hat{q}_2$, $\hat{q}_3$. The projection includes three parts $p_x$, $p_y$, $p_z$ which may be determined as follows:

$p_x = \vec{p} \cdot \hat{q}_1$;

$p_y = \vec{p} \cdot \hat{q}_2$;

$p_z = \vec{p} \cdot \hat{q}_3$;

wherein $\hat{q}_1$, $\hat{q}_2$, $\hat{q}_3$ are unit vectors in the direction of the axes q1,q2,q3 respectively.

As a consequence of the particular relationship between the dipole moment direction and the quadrupolar axes, only one of these projections is non-vanishing and equal in magnitude to the magnitude of the total dipole moment.

Another set of descriptors belonging to the second group are the principal components I1,I2,I3 of moment of inertia referenced to the unit vectors $\hat{q}_1$, $\hat{q}_2$, $\hat{q}_3$. These particular descriptors consist of three diagonal components and three off-diagonal components. The diagonal terms may be determined with respect to unit vectors $\hat{q}_1$, $\hat{i}_2$, $\hat{q}_3$ whose origin is at the center of dipole of the molecule according to the following equations:

$$I'_{11}=\int \rho(\vec{x})\,(x^2+y^2+z^2-x^2)\,d^3x$$

$$I'_{22}=\int \rho(\vec{x})\,(x^2+y^2+z^2-y^2)\,d^3x$$

$$I'_{33}=\int \rho(\vec{x})\,(x^2+y^2+z^2-z^2)\,d^3x$$

wherein $I'_{11}$, $I'_{22}$, $I'_{33}$ represent the moment of inertia of the molecule, $\rho$ is the mass density of the molecule, and x is the vector between the center of dipole of the molecule and the atomic charges of the molecule.

The off-diagonal terms may be determined according to the following equations:

$$I'_{12}=I'_{21}=\int \rho(\vec{x})\,(-xy)\,d^3x$$

$$I'_{13}=I'_{31}=\int \rho(\vec{x})\,(-xz)\,d^3x$$

$$I'_{23}=I'_{32}=\int \rho(\vec{x})\,(-yz)\,d^3x$$

Another descriptor belonging to the second group is the vector displacement of the center of mass of the molecule from the center of dipole of the molecule in the coordinate system defined by the axes q1,q2,q3.

For illustrative purposes only, the present invention as described above includes a novel representation of the quadrupolar component of the multipolar expansion based upon the center of dipole. Importantly, such a representation is most applicable to neutral-dipolar molecules. However, the invention is not limited in this respect and may be broadly applied over the broad range of molecules of differing ionic state, including ions, neutral-polar molecules, neutral-nonpolar-quadrupolar molecules, etc. More specifically, in a more general sense the center of dipole corresponds to a particular "center of N-pole" wherein the center of N-pole is the point in space wherein the next to lowest order non-vanishing multipolar contribution to the electrostatic potential expansion is minimized in the sense previously described. Thus, for ions, the leading non-zero term is the monopole term. In this case the center of N-pole corresponds to the "center of monopole" (or the "center of charge"). More specifically, the center of charge is the point in space wherein the contribution of the dipole moment is exactly zeroed out. For neutral-dipolar molecules as previously discussed wherein the dipole term is the leading nonzero term of the multipolar expansion, the center of N-pole corresponds to the center of dipole. For neutral-quadrupolar molecules wherein the quadrupolar term is the leading nonzero term of the multipolar expansion, the center of N-pole corresponds to the center of quadrupole. More specifically, the center of quadrupole is the point in space wherein the contribution of the octupole moment to the electrostatic potential expansion is minimized.

A more detailed description of the center of charge is now presented. Importantly, the center of charge is applicable to charged molecules. As defined above, the center of charge is the point in space wherein the contribution of the dipole moment is zeroed out. In order to minimize the contribution of the dipolar term $q_{lm}$, note that the dipolar contribution to the multipolar expansion may be represented by the expression:

$$\sum_m |q_{1m}|^2 = \frac{3}{4\pi}\,|\vec{p}|^2$$

wherein p is the dipole moment about an arbitrary point of observation O as described above.

It follows that the molecular dipole is a function of the displacement of the arbitrary point of observation O as follows:

$$\vec{p}\,' = \vec{p} - q\vec{d}$$

wherein a represents the displacement from the arbitrary point of observation O to the center of charge.

Minimizing the dipolar contribution to the multipolar expansion yields $$\frac{\partial}{\partial d_k}\,\Sigma_k(p'_k)^2 = 2\Sigma_k p'_k \frac{\partial p'_k}{\partial d_j}$$

where $$\frac{\partial p'_k}{\partial d_j} = -q\delta_{jk}$$

Thus, $$\frac{\partial}{\partial d_k}\,\Sigma_k p'_k{}^2 = -2q p'_j$$

It follows that the center of charge is where $\vec{p}\,'=0$. In other words, it is defined by $$\vec{d} = \frac{1}{q}\vec{p}$$

This is just a simple charge centroid. In this case, the dipole moment is zero, leaving the net charge term, quadrupolar term and other high order terms of the total multipolar moment. Thus, for charged molecules, the descriptors that characterize the charge distribution of the molecule include the net charge, the principal values of the quadrupole tensor as calculated from the center of charge and the orientation of the principal axes of the quadrupolar tensor as calculated from the center of charge.

Having described the steps necessary to derive descriptors that characterize the shape of a molecule, the charge distribution of the molecule, and the relationship between these descriptors, now consider how the descriptors might be utilized to compare two or more molecules. In summary, the descriptors outlined above may be divided into four categories as follows:

Category I—Shape Descriptors

1] principal components I1,I2,I3 of the moment of inertia of the molecule;

2] orientation of the principal axes (x,y,z) of the moment of inertia of the molecule;

3] the total molecular mass M;

Category II—Charge Descriptors

4] magnitude of dipole moment vector $\vec{p}$;

5] one or more of the principal components (Q1,Q2,Q3) of quadrupole moment tensor Q' about the center of dipole;

6] orientation of principal axes (q1,q2,q3) of the quadrupole moment tensor Q' about the center of dipole;

7] total molecular charge q;

Category III—Shape/Charge Descriptors Referenced to the Inertial Coordinate System 8] projection of the dipole moment vector p onto the principal inertial axes (x,y,z);

9] principal components (Q1,Q2,Q3) of the quadrupole moment tensor Q' referenced to the principal inertial axes (x,y,z) translated such that origin of the axes x,y,z coincide with the center of dipole;

10] the vector displacement of the center of mass of the molecule to the center of dipole of the molecule in the inertial coordinate system as defined by the principal axes x,y,z;

Category IV—Shape/Charge Descriptors Referenced to the Quadrupolar Coordinate System 11] principal components I1,I2,I3 of the moment of inertia tensor I' referenced to the principal axes (q1,q2,q3); and 12] the vector displacement of the center of mass of the molecule to the center of dipole of the molecule in the coordinate system as defined by the principal axes q1,q2,q3.

Figure 9:
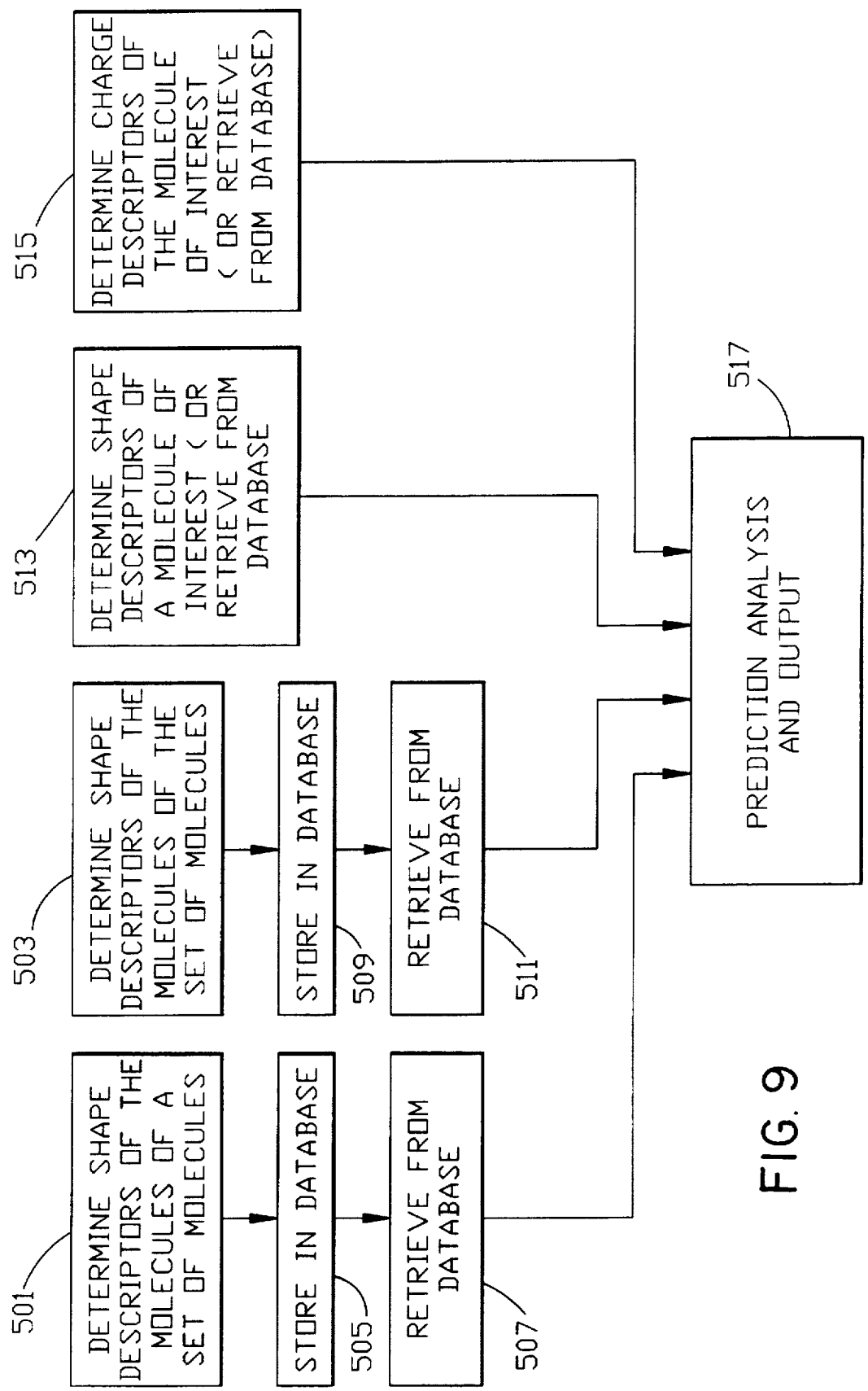
FIG. 9 is a flow chart illustrating the use of the descriptors of the present invention for prediction analysis and output.

The shape and charge descriptors outlined above may be used in similarity searching to determine correspondence between molecules. More specifically, as illustrated in FIG. 9, in step 501 one or more of the shape descriptors as outlined above are determined for a set of molecules. In step 503, one or more of the charge descriptors as outlined above are determined for the set of molecules. The shape and charge descriptors of the set of molecules are preferably stored in a molecular database as information that succinctly describes molecular shape and charge and their relationship, and retrieved therefrom in steps 505,507, 509,511. In step 513, the corresponding shape descriptors of a molecule of interest are determined as described above. In step 515, the corresponding charge descriptors of the molecule of interest are determined as described above. The shape and charge descriptors of the molecule of interest may also be stored in the molecular database, and retrieved therefrom in steps 513 and 515. In step 517, prediction analysis and output is performed whereby the shape and/or charge descriptors of the set of molecules determined in steps 501 and 503 are compared to the corresponding shape and/or charge descriptors determined in steps 513 and 515 to determine a correspondence between the molecule of interest and the set of molecules. The prediction analysis of step 517 may require a direct match of one or more of the descriptors, or may require correspondence of one or more descriptors to be within a predefined limit. In other applications, correspondence may be determined using heuristic analysis of one or more of the descriptors. In step 517, the results of the prediction analysis may be output to the user via the graphical interface 102, or stored in the memory 108 for subsequent processing.

The descriptors may also be utilized in a 3-DQSAR analysis to correlate the shape, charge distribution with measured biological properties of a first set of molecules, typically called a training set, to predict the unknown biological properties of a second set of molecules. A more detailed description of conventional 3-DQSAR techniques may be found in the COMFA Patent, herein incorporated by reference in its entirety, and is also implemented in SYBYL, release 6.01, available from TRIPOS, Inc.

More specifically, one or more parameters representing the biological properties of the molecules of the training set and the descriptors associated with the molecules of the training set are placed in a table. As illustrated in FIG. 10, preferably, the rows of the table correspond to the molecules of the training set wherein each parameter associated with the molecules is allocated a column of the table, and each descriptor D1, D2, D3, ... DN associated with the molecules is allocated a column of the table. Corresponding descriptors are also determined for the second set of molecules having unknown biological properties, and then placed into the table. The parameters and descriptors of the table may be viewed as a system of equations. For instance, consider the case where the first set contains M molecules and the second set contains a single molecule M+1. The following equations can be written:

$$P_1 = C1\,D1(1) + C2\,D2(1) + C3\,D3(1) + \ldots CN\,DN(1)$$
$$P_2 = C1\,D1(2) + C2\,D2(2) + C3\,D3(2) + \ldots CN\,DN(2)$$
$$\vdots$$
$$P_M = C1\,D1(M) + C2\,D2(M) + C3\,D3(M) + \ldots CN\,DN(M)$$
$$P_{M+1} = C1\,D1(M+1) + C2\,D2(M+1) + C3\,D3(M+1) + \ldots CN\,DN(M+1)$$

wherein C1,C2 ... CN are coefficients corresponding to the descriptors D1,D2, ... DN, respectively, D1(1),D2(1) ... DN(1) are descriptors associated with the first molecule of the first set, $P_1$ is a parameter associated with the first molecule of first set, D1(M),D2(M) ... DN(M) are descriptors associated with the $M^{th}$ molecule of the first set, $P_M$ is a parameter associated with the $M^{th}$ molecule of first set, D1(M+1),D2(M+1) ... DN(M+1) are descriptors associated with the (M+1)$^{th}$ molecule of the second set, and $P_{M+1}$ is the unknown parameter associated with the (M+1)$^{th}$ molecule of second set that is to be predicted.

Regression techniques are then applied to the equations pertaining to the M molecules of the training set to solve for the coefficients C1,C2, ... CN. The regression techniques may include PLS as outlined in the COMFA patent or may include more conventional regression techniques as described in Harman, "Modern Factor Analysis," Univ. of Chicago Press, 1960, pp. 155–344, hereinafter incorporated by reference in its entirety. The regression techniques may also include neural network analysis as described in A. C. Good et al., "Structure Activity Relationships from Molecular Similarity Matrices", J. Med. Chem. Vol. 36, 1993, pp. 433–438, and A. N. Jain et al., "Compass: Predicting Biological Activities from Molecular Surface Properties. Performance Comparisons on a Steroid Benchmark", J. Med. Chem. Vol. 37, 1994, pp. 2315–2327, hereinafter incorporated by reference in their entirety.

The coefficients C1,C2 ... CN are then applied to the equation pertaining to the (M+1)$^{th}$ molecule to solve for the unknown parameter $P_{M+1}$. Cross validation as outlined in detail in the COMFA patent may then be utilized to statistically measure the reliability of the solution for the initial M molecules of the training set. Finally, as illustrated in the COMFA patent, the results of the analysis may be output to the user via the graphical interface 102, or stored in the memory 108 for subsequent processing.

Figure 11:
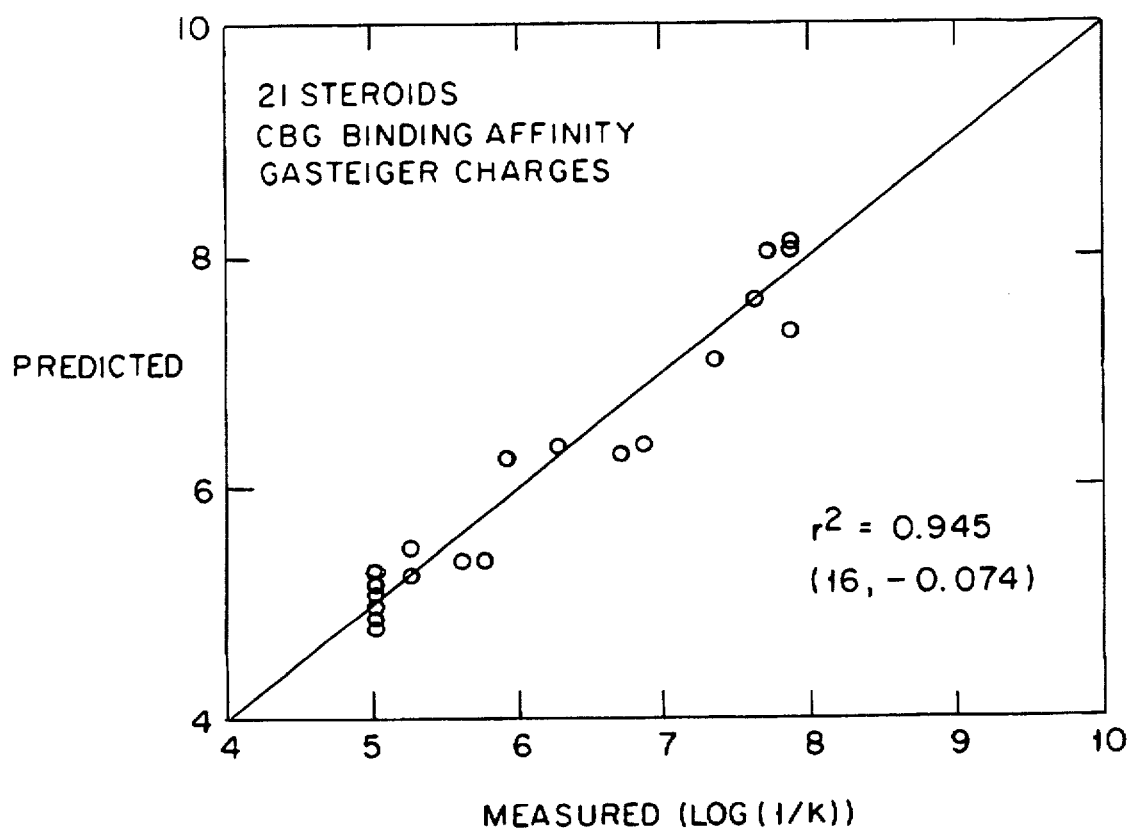
FIG. 11 is a graph illustrating the predicted versus measured values of the CGB binding affinity for 21 steroids as determined utilizing the descriptors of the present invention in a 3-DQSAR analysis.

FIG. 11 illustrates the results obtained by performing 3D-QSAR analysis with seventeen descriptors from first, second and third categories discussed above for a group of twenty-one steroids. The procedure utilized PLS and cross validation by "leaving one out". Note that the correlation between the predicted and measured biological activity for the group, $r^2$, is 0.945, which indicates significant predictive ability.

Moreover, the present invention provides descriptors that efficiently characterize the shape and/or charge distribution of molecules, thus enabling 3-DQSAR analysis based upon a small number of descriptors. This technique may be distinguished from the prior art techniques wherein typically a massive number of descriptors is required for the 3-DQSAR analysis. Advantageously, using a smaller number of descriptors decreases the complexity of the 3-DQSAR analysis, thus improving the processing time required to generate results. Furthermore, in some instances, utilizing a small number of descriptors provides for coefficients of the 3-DQSAR analysis that are not underdetermined. In such cases, the complex PLS analysis may be avoided and substituted with simpler and speedier conventional regression techniques.

In addition, the center of mass and principal inertial axes x,y,z and/or the center of N-pole and the principal axes of the quadrupolar moment tensor Q' calculated about the center of N-pole may be utilized as a reference frame for determining additional descriptors. Such additional descriptors may include, for example, steric and electrostatic energies at grid points, hydrogen bond donor and acceptor locations or van der waals surfaces. These additional descriptors may then be used in prediction analysis or in 3-DQSAR analysis as described above.

For example, the center of mass and principal inertial axes x,y,z and/or the center of N-pole and the principal axes of the quadrupolar moment tensor Q' calculated about the center of N-pole may be utilized as a reference frame to determine additional descriptors by superimposing a grid with respect to the reference frame and assigning the steric and electrostatic energies to each of the grid points as described in the COMFA patent. Importantly, an alignment step is not required when utilizing either the inertial or quadrupolar reference frames.

Other embodiments of the invention will be apparent to those skilled in the art from consideration of the specification and practice of the invention disclosed herein. It is intended that the specification and examples be considered as examples only, with the true scope of the invention being indicated by the claims.

We claim:

1. A program storage device readably by a machine, tangibly embodying a program of instructions executable by the machine to perform method steps for generating and storing data describing physical characteristics of a series of molecules, said method steps comprising the steps of:

for each molecule within said series of molecules,
determining one or more principal components of a moment of inertia tensor of said molecule according to data representing atomic structure of said molecule stored in a memory;
determining orientation of one or more principal axes of said moment of inertia tensor;
assigning said one or more principal components of said moment of inertia tensor to a first descriptor that represents shape of said molecule;
assigning said orientation of said one or more principal axes of said moment of inertia tensor to a second descriptor that represents shape of said molecule; and
storing said first and second descriptors of each molecule in said series of molecules in a database for subsequent processing to thereby identify correspondence between molecules in said series of molecules.

2. The program storage device of claim 1, further comprising the steps of:

for each molecule within said series of molecules,
determining total mass of said molecule according to said data representing atomic structure of said molecule stored in said memory;
assigning said total mass of said molecule to a third descriptor that represents shape of said molecule; and
storing said third descriptor of each molecule in said series of molecules in said database for subsequent processing to thereby identify correspondence between molecules in said series of molecules.

3. The program storage device of claim 1, wherein said series of molecules comprises a first set of molecules and a second set of molecules,
wherein each particular molecule of said first set is associated with a first parameter representing a measured biological property of said particular molecule of said first set, said first parameter defined by a first series of terms including terms that correspond to said first and second descriptors assigned to said particular molecule of said first set and additional descriptors assigned to said particular molecule of said first set and that are defined by operation of a coefficient upon the corresponding descriptor;
wherein each particular molecule of said second set is associated with a second parameter representing a predicted biological property of said particular molecule of said second set, said second parameter defined by a second series of terms including terms that correspond to said first and second descriptors assigned to said particular molecule of said second set and additional descriptors assigned to said particular molecule of said second set and that are defined by operation of a coefficient upon the corresponding descriptor, wherein said coefficients of said terms of said second series are identical to said coefficients of said terms of said first series, further comprising the step of:

for each particular molecule within said second set of molecules,
solving for said coefficients of said terms of said first series and said second series,
adding said terms of said second series to determine said second parameter.

4. The program storage device of claim 3, wherein the solving step utilizes partial least squares regression analysis.

5. The program storage device of claim 3, wherein the solving step utilizes conventional regression analysis.

6. A program storage device readably by a machine, tangibly embodying a program of instructions executable by the machine to Perform method steps for determining correspondence between molecules in a series of molecules based upon data describing physical characteristics of said series of molecules stored in memory, said method steps comprising the steps of:

for each molecule within said series of molecules,
retrieving from memory first data representing one or more principal components of a moment of inertia tensor of said molecule;
retrieving from memory second data representing orientation of principal axes of said moment of inertia tensor;
assigning said first data to a first descriptor that represents shape of said molecule;
assigning said second data to a second descriptor that represents shape of said molecule: and
determining correspondence between molecules of said series of molecules according to said first and second descriptors.

7. The program storage device of claim 6, further comprising the steps of:

for each molecule within said series of molecules,
retrieving from memory third data representing total mass of said molecule;
assigning said third data to a third descriptor that represents shape of said molecule; and
determining correspondence between molecules of said series of molecules according to said third descriptors.

8. The program storage device of claim 6, wherein said series of molecules comprises a first set of molecules and a second set of molecules, wherein each particular molecule of said first set is associated with a first parameter representing a measured biological property of said particular molecule of said first set, said first parameter defined by a first series of terms including terms that correspond to said first and second descriptors assigned to said particular molecule of said first set and additional descriptors assigned to said particular molecule of said first set and that are defined by operation of a coefficient upon the corresponding descriptor;

wherein each particular molecule of said second set is associated with a second parameter representing a predicted biological property of said particular molecule of said second set, said second parameter defined by a second series of terms including terms that correspond to said first and second descriptors assigned to said particular molecule of said second set and additional descriptors assigned to said particular molecule of said second set and that are defined by operation of a coefficient upon the corresponding descriptor, wherein said coefficients of said terms of said second series are identical to said coefficients of said terms of said first series, further comprising the step of:

for each particular molecule within said second set of molecules,
solving for said coefficients of said terms of said first series and said second series,
adding said terms of said second series to determine said second parameter.

9. A program storage device readably by a machine, tangibly embodying a program of instructions executable by the machine to perform method steps for generating and storing data describing physical characteristics of a series of molecules said method steps comprising the steps of:

for each molecule within said series of molecules, 'determining one or more components of a second ranked tensor that describes charge distribution of said molecule according to data representing atomic structure and atomic charge of said molecule stored in a memory;
assigning said one or more components of said second ranked tensor to a first descriptor that represents charge distribution of said molecules and
storing said first descriptor of each molecule in said series of molecules in a database for subsequent processing to thereby identify correspondence between molecules in said series of molecules.

10. The program storage device of claim 9, wherein said second ranked tensor represents a quadrupolar moment tensor of said molecule about a center of N-pole, wherein said center of N-pole corresponds to a point in space wherein the next to lowest order non-zero multipolar contribution to the electrostatic potential expansion is minimized.

11. The program storage device of claim 10, wherein said center of N-pole is center of dipole.

12. The program storage device of claim 10, wherein said center of N-pole is center of charge.

13. The program storage device of claim 10, wherein said one or more components of said second rank tensor are principal components.

14. The program storage device of claim 13, further comprising the steps of:

for each molecule within said series of molecules,
determining orientation of principal axes of said second rank tensor;
assigning said orientation of said principal axes of said second ranked tensor to a second descriptor that represents charge distribution of said molecule; and
storing said second descriptor of each molecule in said series of molecules in a database for subsequent processing to thereby identify correspondence between molecules in said series of molecules.

15. The program storage device of claim 9, further comprising the steps of:

for each molecule within said series of molecules,
determining dipole moment of said molecule according to said data representing atomic structure and atomic charge of said molecule stored in said memory;
assigning said dipole moment of said molecule to a second descriptor that represents charge distribution of said molecule; and
storing said second descriptor of each molecule in said series of molecules in a database for subsequent processing to thereby identify correspondence between molecules in said series of molecules.

16. The program storage device of claim 9,
wherein said series of molecules comprises a first set of molecules and a second set of molecules,
wherein each particular molecule of said first set is associated with a first parameter representing a measured biological property of said particular molecule of said first set, said first parameter defined by a first series of terms including terms that correspond to said first descriptor assigned to said particular molecule of said first set and additional descriptors assigned to said particular molecule of said first set and that are defined by operation of a coefficient upon the corresponding descriptor;
wherein each particular molecule of said second set is associated with a second parameter representing a predicted biological property of said particular molecule of said second set, said second parameter defined by a second series of terms including terms that correspond to said first descriptor assigned to said particular molecule of said second set and additional descriptors assigned to said particular molecule of said second set and that are defined by operation of a coefficient upon the corresponding descriptor, wherein said coefficients of said terms of said second series are identical to said coefficients of said terms of said first series,
further comprising the step of:
for each particular molecule within said second set of molecules,
solving for said coefficients of said terms of said first series and said second series,
adding said terms of said second series to determine said second parameter.

17. A program storage device readably by a machine, tangibly embodying a program of instructions executable by the machine to perform method steps for determining correspondence between molecules in a series of molecules based upon data describing physical characteristics of said series of molecules stored in memory, said method steps comprising the steps of:
for each molecule within said series of molecules,
retrieving from memory first data representing one or more components of a second ranked tensor that describes charge distribution of said molecule;
assigning said first data to a first descriptor that represents charge distribution of said molecule; and
determining correspondence between molecules of said series of molecules according to said first descriptors.

18. The program storage device of claim 17, wherein said second ranked tensor represents a quadrupolar moment tensor of said molecule about a center of N-pole, wherein said center of N-pole corresponds to a point in space wherein the next to lowest order non-zero multipolar contribution to the electrostatic potential expansion is minimized.

19. The program storage device of claim 18, wherein said center of N-pole is center of dipole.

20. The program storage device of claim 18, wherein said center of N-pole is center of charge.

21. The program storage device of claim 18, wherein said one or more components of said second rank tensor are principal components.

22. The program storage device of claim further comprising the steps of:
for each molecule within said series of molecules,
retrieving from memory second data representing orientation of principal axes of said second ranked tensor;
assigning said second data to a second descriptor that represents charge distribution of said molecule; and
determining correspondence between molecules of said series of molecules according to said second descriptors.

23. The program storage device of claim 18,
wherein said series of molecules comprises a first set of molecules and a second set of molecules,
wherein each particular molecule of said first set is associated with a first parameter representing a measured biological property of said particular molecule of said first set, said first parameter defined by a first series of terms including terms that correspond to said first descriptor assigned to said particular molecule of said first set and additional descriptors assigned to said particular molecule of said first set and that are defined by operation of a coefficient upon the corresponding descriptor;
wherein each particular molecule of said second set is associated with a second parameter representing a predicted biological property of said particular molecule of said second set, said second parameter defined by a second series of terms including terms that correspond to said first descriptor assigned to said particular molecule of said second set and additional descriptors assigned to said particular molecule of said second set and that are defined by operation of a coefficient upon the corresponding descriptor, wherein said coefficients of said terms of said second series are identical to said coefficients of said terms of said first series,
further comprising the step of:
for each particular molecule within said second set of molecules,
solving for said coefficients of said terms of said first series and said second series,
adding said terms of said second series to determine said second parameter.

24. The program storage device of claim 17,
wherein said series of molecules comprises a first set of molecules and a second set of molecules,
wherein each particular molecule of said first set is associated with a first parameter representing a measured biological property of said particular molecule of said first set, said first parameter defined by a first series of terms including terms that correspond to said first descriptor assigned to said particular molecule of said first set and additional descriptors assigned to said particular molecule of said first set and that are defined by operation of a coefficient upon the corresponding descriptor;
wherein each particular molecule of said second set is associated with a second parameter representing a predicted biological property of said particular molecule of said second set, said second parameter defined by a second series of terms including terms that correspond to said first descriptor assigned to said particular molecule of said second set and additional descriptors assigned to said particular molecule of said second set and that are defined by operation of a coefficient upon the corresponding descriptor, wherein said coefficients of said terms of said second series are identical to said coefficients of said terms of said first series,
further comprising the step of:
for each particular molecule within said second set of molecules,
solving for said coefficients of said terms of said first series and said second series, adding said terms of said second series to determine said second parameter.

25. The program storage device of claim 17, further comprising the steps of:

for each molecule within said series of molecules,
retrieving from memory second data representing one or more components of a second ranked tensor representing shape of said molecule;
assigning said second data to a second descriptor that represents shape of said molecule and
determining correspondence between molecules of said series of molecules according to said second descriptors.

26. The program storage device of claim 25, wherein said second ranked tensor representing shape of said molecule represents moment of inertia tensor of said molecule, and wherein said second ranked tensor representing charge distribution represents a quadrupolar moment tensor of said molecule about a center of N-pole, wherein said center of N-pole corresponds to a point in space wherein the next to lowest order non-zero multipolar contribution to the electrostatic potential expansion is minimized.

27. The program storage device of claim 26, wherein said center of N-pole is center of dipole.

28. The program storage device of claim 26, wherein said center of N-pole is center of charge.

29. The program storage device of claim 26, wherein said series of molecules comprises a first set of molecules and a second set of molecules, wherein each particular molecule of said first set is associated with a first parameter representing a measured biological property of said particular molecule of said first set, said first parameter defined by a first series of terms including terms that correspond to said first and second descriptors assigned to said particular molecule of said first set and additional descriptors assigned to said particular molecule of said first set and that are defined by operation of a coefficient upon the corresponding descriptor;

wherein each particular molecule of said second set is associated with a second parameter representing a predicted biological property of said particular molecule of said second set, said second parameter defined by a second series of terms including terms that correspond to said first and second descriptors assigned to said particular molecule of said second set and additional descriptors assigned to said particular molecule of said second set and that are defined by operation of a coefficient upon the corresponding descriptor, wherein said coefficients of said terms of said second series are identical to said coefficients of said terms of said first series, further comprising the steps of:
for each particular molecule within said second set of molecules,
solving for said coefficients of said terms of said first series and said second series,
adding said terms of said second series to determine said second parameter.

30. The program storage device of claim 26, further comprising the steps of:

for each molecule within said series of molecules,
retrieving from memory third data defining relationship between shape and charge distribution of said molecule; and
assigning said third data to a third descriptor;
wherein said third data represents at least one of the following:
projection of a dipole moment of said molecule onto principle inertial axes of said molecule;
one or more of said principal components of said quadrupolar moment tensor referenced to principal inertial axes of said molecule translated such that origin of said principal inertial axes coincide with said center of N-pole; and
displacement between center of mass of said molecule and said center of N-pole; and
determining correspondence between molecules of said series of molecules according to said third descriptors.

31. The program storage device of claim 30, wherein said series of molecules comprises a first set of molecules and a second set of molecules, wherein each particular molecule of said first set is associated with a first parameter representing a measured biological property of said particular molecule of said first set, said first parameter defined by a first series of terms including terms that correspond to said first and second descriptors assigned to said particular molecule of said first set and additional descriptors assigned to said particular molecule of said first set and that are defined by operation of a coefficient upon the corresponding descriptor;

wherein each particular molecule of said second set is associated with a second parameter representing a predicted biological property of said particular molecule of said second set, said second parameter defined by a second series of terms including terms that correspond to said first and second descriptors assigned to said particular molecule of said second set and additional descriptors assigned to said particular molecule of said second set and that are defined by operation of a coefficient upon the corresponding descriptor, wherein said coefficients of said terms of said second series are identical to said coefficients of said terms of said first series, further comprising the steps of:
for each particular molecule within said second set of molecules,
solving for said coefficients of said terms of said first series and said second series,
adding said terms of said second series to determine said second parameter.

32. The program storage device of claim 25, further comprising the steps of:

for each molecule within said series of molecules,
retrieving from memory third data defining relationship between shape and charge distribution of said molecule; and
assigning said third data to a third descriptors and
determining correspondence between molecules of said series of molecules according to said third descriptors.

33. The program storage device of claim 32, wherein said series of molecules comprises a first set of molecules and a second set of molecules, wherein each particular molecule of said first set is associated with a first parameter representing a measured biological property of said particular molecule of said first set, said first parameter defined by a first series of terms including terms that correspond to said first and second descriptors assigned to said particular molecule of said first set and additional descriptors assigned to said particular molecule of said first set and that are defined by operation of a coefficient upon the corresponding descriptor;

wherein each particular molecule of said second set is associated with a second parameter representing a predicted biological property of said particular molecule of said second set, said second parameter defined by a second series of terms including terms that correspond to said first and second descriptors assigned to said particular molecule of said second set and additional descriptors assigned to said particular molecule of said second set and that are defined by operation of a coefficient upon the corresponding descriptor, wherein said coefficients of said terms of said second series are identical to said coefficients of said terms of said first series, further comprising the steps of:
for each particular molecule within said second set of molecules,
solving for said coefficients of said terms of said first series and said second series,
adding said terms of said second series to determine said second parameter.

34. A program storage device readably by a machine, tangibly embodying a program of instructions executable by the machine to perform method steps for generating and storing data describing physical characteristics of a series of molecules, said method steps comprising the steps of:

for each molecule within said series of molecules, determining a coordinate system defined by
principle axes of a second ranked tensor representing one of shape and charge distribution of said molecule according to data representing atomic structure of said molecule stored in memory; and
determining a descriptor representing said one of shape and charge distribution of said molecule, wherein said descriptor is referenced to said coordinate system and
storing said descriptors of each molecule in said series of molecules in a database for subsequent processing to thereby identify correspondence between molecules in said series of molecules.

35. The program storage device of claim 34, wherein said second ranked tensor represents moment of inertia of said molecule.

36. The program storage device of claim 34, wherein said second ranked tensor represents a quadrupolar moment tensor of said molecule about a center of N-pole, wherein said center of N-pole corresponds to a point in space wherein the next to lowest order non-zero multipolar contribution to the electrostatic potential expansion is minimized.

37. The program storage device of claim 34, wherein said series of molecules comprises a first set of molecules and a second set of molecules, wherein each particular molecule of said first set is associated with a first parameter representing a measured biological property of said particular molecule of said first set, said first parameter defined by a first series of terms including terms that correspond to said descriptor assigned to said particular molecule of said first set and additional descriptors assigned to said particular molecule of said first set and that are defined by operation of a coefficient upon the corresponding descriptor;

wherein each particular molecule of said second set is associated with a second parameter representing a predicted biological property of said particular molecule of said second set, said second parameter defined by a second series of terms including terms that correspond to said descriptor assigned to said particular molecule of said second set and additional descriptors assigned to said particular molecule of said second set and that are defined by operation of a coefficient upon the corresponding descriptor, wherein said coefficients of said terms of said second series are identical to said coefficients of said terms of said first series, further comprising the steps of:
for each particular molecule within said second set of molecules,
solving for said coefficients of said terms of said first series and said second series,
adding said terms of said second series to determine said second parameter.

* * * * *

UNITED STATES PATENT AND TRADEMARK OFFICE
CERTIFICATE OF CORRECTION

PATENT NO. : 5,784,294
DATED : July 21, 1998
INVENTOR(S) : D. E. Platt et al.

It is certified that error appears in the above-identified patent and that said Letters Patent is hereby corrected as shown below:

In Col. 18, line 13 (line 1 of claim 1), change "readably" to --readable--.
In Col. 19, line 19 (line 1 of claim 6), change "readably" to --readable--.
In Col. 20, line 14 (line 1 of claim 9), change "readably" to --readable--;
    line 19 (line 6 of claim 9), before "determining", delete --'--;
    line 20 (line 7 of claim 9), change "ranked" to --rank--;
    line 25 (line 12 of claim 9), change "ranked" to --rank--;
    line 32 (line 2 of claim 10), change "ranked" to --rank--; and
    line 51 (line 7 of claim 14), change "ranked" to --rank--.
In Col. 21, line 34 (line 1 of claim 17), change "readably" to --readable--;
    line 43 (line 10 of claim 17), change "ranked" to --rank--;
    line 50 (line 2 of claim 18), change "ranked" to --rank--;
    line 62 (line 1 of claim 22), after "claim" add --21--; and
    line 66 (line 5 of claim 22), change "ranked" to --rank--.

UNITED STATES PATENT AND TRADEMARK OFFICE
CERTIFICATE OF CORRECTION

PATENT NO. : 5,784,294
DATED : July 21, 1998
INVENTOR(S) : D.E. Platt et al.

It is certified that error appears in the above-identified patent and that said Letters Patent is hereby corrected as shown below:

In Col. 23, line 7 (line 5 of claim 25), change "ranked" to --rank--;
    line 15 (line 2 of claim 26), change "ranked" to --rank--; and
    line 17 (line 4 of claim 26), change "ranked" to --rank--.
In Col. 25, line 23 (line 1 of claim 34), change "readably" to --readable--; and
    line 30 (line 10 of claim 34), change "ranked" to --rank--.
In Col. 26, line 2 (line 2 of claim 35), change "ranked" to --rank--; and
    line 5 (line 2 of claim 36), change "ranked" to --rank--.

Signed and Sealed this

Thirteenth Day of April, 1999

Attest:

Q. TODD DICKINSON

*Attesting Officer*      *Acting Commissioner of Patents and Trademarks*